United States Patent
Menkhaus et al.

(10) Patent No.: US 10,293,289 B2
(45) Date of Patent: *May 21, 2019

(54) HYBRID FELTS OF ELECTROSPUN NANOFIBERS

(71) Applicant: Nanopareil, LLC, Dakota Dunes, SD (US)

(72) Inventors: Todd J. Menkhaus, Dakota Dunes, SD (US); Hao Fong, Dakota Dunes, SD (US)

(73) Assignee: Nanopareil, LLC, Dakota Dunes, SD (US)

(*) Notice: Subject to any disclaimer, the term of this patent is extended or adjusted under 35 U.S.C. 154(b) by 122 days.

This patent is subject to a terminal disclaimer.

(21) Appl. No.: 15/434,180

(22) Filed: Feb. 16, 2017

(65) Prior Publication Data

US 2017/0157544 A1    Jun. 8, 2017

Related U.S. Application Data

(63) Continuation of application No. 14/000,981, filed as application No. PCT/US2013/026233 on Feb. 14, 2013, now Pat. No. 9,604,168.

(51) Int. Cl.
*B01D 39/16* (2006.01)
*B01D 39/04* (2006.01)
(Continued)

(52) U.S. Cl.
CPC ....... *B01D 39/1615* (2013.01); *B01D 15/327* (2013.01); *B01D 15/361* (2013.01);
(Continued)

(58) Field of Classification Search
CPC .......................... B01D 15/327; B01D 15/361; B01D 15/3809; B01D 37/39; B01D 37/00;
(Continued)

(56) References Cited

U.S. PATENT DOCUMENTS 3,524,221 A    8/1970  Jones, Jr.
3,547,763 A   12/1970  Hoffman, Jr.
(Continued)

FOREIGN PATENT DOCUMENTS

CN    101203927 A    6/2008
EP      0251729 B1    1/1988
(Continued)

OTHER PUBLICATIONS

Zhang, Lifeng et al., "Fabrication and Bioseparation Studies of Adsorptive Membranes/Felts made from Electrospun Cellulose Acetate Nanofibers", Journal of Membrane Science, 319, (2008) pp. 176-184. Mar. 27, 2008.

(Continued)

*Primary Examiner* — Joseph W Drodge
(74) *Attorney, Agent, or Firm* — McKee, Voorhees & Sease, PLC (57) ABSTRACT

The present invention relates generally to compositions for use in biological and chemical separations, as well as other applications. More specifically, the present invention relates to hybrid felts fabricated from electrospun nanofibers with high permeance and high capacity. Such hybrid felts utilize derivatized cellulose, and at least one non-cellulose-based polymer that may be removed from the felt by subjecting it to moderately elevated temperatures and/or solvents capable of dissolving the non-cellulose-based polymer to leave behind a porous nanofiber felt having more uniform pore sizes and other enhanced properties when compared to single component nanofiber felts.

20 Claims, 1 Drawing Sheet

(51) Int. Cl.
| | |
|---|---|
| *D01D 5/00* | (2006.01) |
| *B01D 39/18* | (2006.01) |
| *B01D 71/16* | (2006.01) |
| *B01J 20/32* | (2006.01) |
| *H01L 23/48* | (2006.01) |
| *H01L 23/00* | (2006.01) |
| *H01L 25/065* | (2006.01) |
| *H01L 25/00* | (2006.01) |
| *D01F 2/24* | (2006.01) |
| *D01F 6/44* | (2006.01) |
| *D01F 6/88* | (2006.01) |
| *B01D 15/32* | (2006.01) |
| *B01D 15/36* | (2006.01) |
| *B01J 20/24* | (2006.01) |
| *B01J 20/28* | (2006.01) |
| *B01D 15/38* | (2006.01) |
| *C07K 1/22* | (2006.01) |

(52) U.S. Cl.
CPC ..... *B01D 15/3809* (2013.01); *B01D 39/1623* (2013.01); *B01D 39/1676* (2013.01); *B01J 20/24* (2013.01); *B01J 20/28007* (2013.01); *B01J 20/28038* (2013.01); *B01J 20/3212* (2013.01); *B01J 20/3217* (2013.01); *B01J 20/3248* (2013.01); *B01J 20/3293* (2013.01); *C07K 1/22* (2013.01); *D01D 5/003* (2013.01); *D01D 5/0007* (2013.01); *D01F 2/24* (2013.01); *D01F 6/44* (2013.01); *D01F 6/88* (2013.01); *H01L 23/48* (2013.01); *H01L 24/72* (2013.01); *H01L 24/73* (2013.01); *H01L 24/90* (2013.01); *H01L 24/91* (2013.01); *H01L 25/0652* (2013.01); *H01L 25/50* (2013.01); *B01D 15/3804* (2013.01); *B01D 2239/025* (2013.01); *B01D 2239/0414* (2013.01); *H01L 24/16* (2013.01); *H01L 2224/131* (2013.01); *H01L 2224/16227* (2013.01); *H01L 2224/73201* (2013.01); *H01L 2224/81138* (2013.01); *H01L 2224/81815* (2013.01); *H01L 2224/9211* (2013.01); *H01L 2225/06517* (2013.01); *H01L 2225/06527* (2013.01); *H01L 2225/06531* (2013.01); *H01L 2225/06562* (2013.01); *H01L 2225/06593* (2013.01); *H01L 2924/0002* (2013.01); *H01L 2924/157* (2013.01); *H01L 2924/1579* (2013.01); *H01L 2924/15153* (2013.01); *H01L 2924/15787* (2013.01); *H01L 2924/15788* (2013.01); *H01L 2924/3511* (2013.01); *H01L 2924/37001* (2013.01)

(58) Field of Classification Search
CPC ........ B01D 37/02; B01D 37/04; B01D 37/16; B01D 37/1607; B01D 37/1615; B01D 37/1623; B01D 37/1669; B01D 37/1676; B01D 37/18; B01D 71/06; B01D 71/08; B01D 71/10; B01D 71/12; B01D 71/14; B01D 71/16; B01D 71/18; B01D 71/20; B01D 71/22; B01D 71/76; B01D 2239/0208; B01D 2239/0216; B01D 2239/0241; B01D 2239/0266; B01D 2239/025; B01D 2239/04; B01D 2239/0407; B01D 2239/0631; B01D 2239/0636; B01D 2239/064; B01D 2239/12; B01D 2221/10; B01D 2323/39; B01D 39/00; B01D 39/02; B01D 39/04; B01D 39/16; B01D 39/1607; B01D 39/1615; B01D 39/1623; B01D 39/1669; B01D 39/1676; B01D 39/18; B32B 27/00; B32B 27/02; B32B 27/04; B32B 27/12; B32B 27/28; B32B 27/281; B32B 27/34; B32B 27/36; B32B 27/40; B32B 38/0008; D01D 5/00; D01D 5/0007; D01D 5/0061; D01D 5/0069; D01D 5/0084; D01D 5/003; D04H 1/00; D04H 1/425; D04H 1/4266; D04H 1/4334; D04H 1/4342; D04H 3/005; D04H 3/007; D04H 5/00; H01L 24/16; H01L 24/72; H01L 24/73; H01L 24/90; H01L 24/91; H01L 25/50; H01L 2924/15153; H01L 2924/157; H01L 2924/15787; H01L 2224/131; H01L 2224/16227; H01L 2224/73201; H01L 2224/81138; H01L 2224/81815; H01L 2224/9211; H01L 2225/06517; H01L 2225/06527; H01L 2225/06531; H01L 2225/06562; H01L 2225/06593; H01L 2924/0002; H01L 2924/37001; H01L 2924/15788; H01L 2924/1579; B01J 20/24; B01J 20/28007; B01J 20/28038; B01J 20/3212; B01J 20/3217; B01J 20/3293; C07K 1/22; D01F 2/24; D01F 6/44; D01F 6/88
USPC ....... 210/767, 503, 505, 508, 502.1, 500.27, 210/500.28, 500.29, 500.3, 500.36, 210/500.38, 500.39; 264/465, 466; 428/213, 221, 361, 375, 376
See application file for complete search history.

(56) References Cited

U.S. PATENT DOCUMENTS

| | | |
|---|---|---|
| 3,560,603 A | 2/1971 | Ryan, Jr. |
| 3,640,308 A | 2/1972 | Bydal |
| 3,868,870 A | 3/1975 | Anthony et al. |
| 3,985,714 A | 10/1976 | Kidder |
| 4,137,032 A | 1/1979 | Honnaker et al. |
| 4,168,250 A * | 9/1979 | Sutthoff .................. B01J 20/22 210/679 |
| 4,316,711 A | 2/1982 | Wellborn |
| 4,384,957 A | 5/1983 | Crowder, III et al. |
| 4,518,440 A | 5/1985 | Phillips, Jr. |
| 4,842,503 A | 6/1989 | Judge |
| 5,011,541 A | 4/1991 | Leech |
| 5,176,926 A | 1/1993 | Tung |
| 5,234,645 A | 8/1993 | Grindstaff |
| 5,922,366 A | 7/1999 | Short |
| 6,169,045 B1 | 1/2001 | Pike et al. |
| 6,717,699 B1 | 4/2004 | Janssen et al. |
| 6,822,073 B2 | 11/2004 | Quirk |
| 6,945,249 B2 | 9/2005 | Griesbach, III et al. |
| 6,948,499 B2 | 9/2005 | Griesbach, III et al. |
| 6,998,462 B2 | 2/2006 | Duan et al. |
| RE39,246 E | 8/2006 | Putzig |
| 7,179,603 B2 | 2/2007 | Quirk |
| 7,547,662 B1 | 6/2009 | Quirk |
| 7,592,277 B2 | 9/2009 | Andrady et al. |
| 7,655,070 B1 | 2/2010 | Dallas et al. |
| 7,927,540 B2 | 4/2011 | Smithies et al. |
| 8,088,323 B2 | 1/2012 | Hellring et al. |
| 8,241,729 B2 | 8/2012 | Conley et al. |
| 8,253,971 B2 | 8/2012 | Von Spreckelsen et al. |
| 8,282,712 B2 | 10/2012 | Chi et al. |
| 8,298,657 B2 | 10/2012 | Bonner et al. |
| 8,403,151 B2 | 3/2013 | Cheng et al. |
| 8,470,722 B2 | 6/2013 | Conley et al. |
| 8,679,216 B2 | 3/2014 | Schelling et al. |
| 9,012,010 B2 | 4/2015 | Yano et al. |
| 9,180,393 B2 | 11/2015 | Chen et al. |
| 9,259,455 B2 | 2/2016 | Song et al. |
| 9,458,452 B2 | 10/2016 | Singer et al. |

(56) References Cited

U.S. PATENT DOCUMENTS

| | | | |
|---|---|---|---|
| 9,604,168 B2* | 3/2017 | Menkhaus | H01L 23/48 |
| 9,623,352 B2 | 4/2017 | Kas et al. | |
| 2004/0241436 A1 | 12/2004 | Hsieh et al. | |
| 2006/0091068 A1* | 5/2006 | Nieland | B01D 39/04 |
| | | | 210/503 |
| 2006/0264140 A1 | 11/2006 | Andrady et al. | |
| 2007/0125700 A1* | 6/2007 | Ding | B01D 39/083 |
| | | | 210/490 |
| 2007/0125703 A1* | 6/2007 | Chapman | B01D 39/083 |
| | | | 210/504 |
| 2007/0237800 A1 | 10/2007 | Lahann | |
| 2007/0246419 A1* | 10/2007 | Milosavljevic | B01D 46/0023 |
| | | | 210/284 |
| 2008/0160856 A1 | 7/2008 | Chen et al. | |
| 2008/0217239 A1 | 9/2008 | Chen et al. | |
| 2008/0265469 A1 | 10/2008 | Li et al. | |
| 2008/0274658 A1 | 11/2008 | Simmonds et al. | |
| 2008/0296808 A1 | 12/2008 | Joo et al. | |
| 2009/0026137 A1 | 1/2009 | Chen et al. | |
| 2009/0065436 A1 | 3/2009 | Kalayci et al. | |
| 2009/0255226 A1 | 10/2009 | Kohli et al. | |
| 2011/0117319 A1 | 5/2011 | Yano et al. | |
| 2011/0180951 A1 | 7/2011 | Teo et al. | |
| 2011/0198282 A1 | 8/2011 | Chu et al. | |
| 2012/0029654 A1 | 2/2012 | Xu et al. | |
| 2012/0061332 A1 | 3/2012 | Kas et al. | |
| 2012/0241391 A1 | 9/2012 | Carlson et al. | |
| 2012/0258160 A1 | 10/2012 | Song et al. | |
| 2013/0092622 A1 | 4/2013 | Kas et al. | |
| 2014/0116945 A1 | 5/2014 | Kas et al. | |
| 2014/0287230 A1 | 9/2014 | Walls et al. | |
| 2015/0056471 A1 | 2/2015 | Joo et al. | |
| 2016/0308184 A1 | 10/2016 | Joo et al. | |

FOREIGN PATENT DOCUMENTS

| | | |
|---|---|---|
| EP | 0317273 A2 | 5/1989 |
| EP | 0341978 B2 | 11/1989 |
| EP | 0341979 B1 | 11/1989 |
| EP | 0452907 B1 | 10/1991 |
| EP | 0552274 B1 | 7/1993 |
| EP | 0619849 B1 | 10/1994 |
| EP | 0729375 B1 | 9/1996 |
| EP | 0950133 B1 | 10/1999 |
| EP | 1137829 B2 | 10/2001 |
| EP | 1149198 B1 | 10/2001 |
| EP | 1299581 B1 | 4/2003 |
| EP | 1322802 B1 | 7/2003 |
| EP | 1333731 B1 | 8/2003 |
| EP | 1345635 B1 | 9/2003 |
| EP | 1370617 B1 | 12/2003 |
| EP | 1782715 A1 | 5/2007 |
| EP | 1834019 B1 | 9/2007 |
| EP | 2077733 B1 | 7/2009 |
| EP | 2083644 B1 | 8/2009 |
| EP | 2088881 B1 | 8/2009 |
| EP | 2131689 B1 | 12/2009 |
| EP | 2160778 B1 | 3/2010 |
| EP | 2231391 B1 | 9/2010 |
| EP | 2724672 A1 | 4/2014 |
| RU | 2439216 C2 | 4/2011 |
| RU | 2009135761 A | 4/2011 |
| WO | 9402667 A1 | 2/1994 |
| WO | 9825979 A1 | 6/1998 |
| WO | 9838358 A1 | 9/1998 |
| WO | 0012789 A1 | 3/2000 |
| WO | 0037385 A1 | 6/2000 |
| WO | 0144500 A2 | 6/2001 |
| WO | 0145280 A1 | 6/2001 |
| WO | 02068497 A1 | 9/2002 |
| WO | 03090928 A1 | 11/2003 |
| WO | 2005077528 A1 | 8/2005 |
| WO | 2005092013 A2 | 10/2005 |
| WO | 2006049663 A1 | 5/2006 |
| WO | 2006049664 A1 | 5/2006 |
| WO | 2008063298 A2 | 5/2008 |
| WO | 2008070159 A2 | 6/2008 |
| WO | 2008099140 A2 | 8/2008 |
| WO | 2009140381 A1 | 11/2009 |
| WO | 2010014980 A2 | 2/2010 |
| WO | 2010014986 A2 | 2/2010 |
| WO | 2010042647 A2 | 4/2010 |
| WO | 2010059280 A4 | 5/2010 |
| WO | 2010077718 A2 | 7/2010 |
| WO | 2010107503 A1 | 9/2010 |
| WO | 2012135679 A2 | 10/2012 |
| WO | 2013013241 A2 | 1/2013 |
| WO | 2013135360 A1 | 9/2013 |
| WO | 2014093345 A1 | 6/2014 |
| WO | 2015052465 A1 | 4/2015 |
| WO | 2015097236 A2 | 7/2015 |
| WO | 2015124250 A1 | 8/2015 |
| WO | 2015124739 A1 | 8/2015 |
| WO | 2015188910 A1 | 12/2015 |
| WO | 2015200239 A1 | 12/2015 |
| WO | 2016007345 A1 | 1/2016 |
| WO | 2016036508 A1 | 3/2016 |
| WO | 2016167871 A1 | 10/2016 |

OTHER PUBLICATIONS

Schneiderman, Steven et al., "Mathematical Model Using Non-Uniform Flow Distribution for Dynamic Protein Breakthrough with Membrane Adsorption Media", Journal of Chromatography A, 1218 (2011), pp. 9121-9127. Oct. 28, 2011.

Ma, Zuwei et al., "Electrospun Regenerated Cellulose Nanofiber Affinity Membrane Functionalized with Protein A/G for IgG Purification", Journal of Membrane Science, 319 (2008), pp. 23-28. Mar. 30, 2008.

Ma, Zuwei et al., "Electrospun Cellulose Nanofiber as Affinity Membrane", Journal of Membrane Science 265 (2005) pp. 115-123. Jun. 23, 2005.

Varadaraju, Hemanthram et al., "Process and Economic Evaluation for Monoclonal Antibody Purification Using a Membrane-Only Process", American Institute of Chemical Engineers, (2011), pp. 1297-1305. May 26, 2011.

Gorley, Stephan V., Editor, "Handbook of Membrane Research Properties, Performance and Applications", Chemical Engineering Methods and Technology Series, pp. 105-135. 2010.

Khatri, Zeeshan, et al, "Effect of Deacetylation on Wicking Behavior of Co-Electrospun Cellulose Acetate/Polyvinyl Alcohol Nanofibers Blend", Carbohydrate Polymers (2012) 87: pp. 2183-2188.

Webster, Martial, et al., "Tunable Thermo-Responsive Poly(N-vinylcaprolactam) Cellulose Nanofibers: Synthesis, Characterization, and Fabrication", Macromol. Mater. Eng. (2013) 298, pp. 447-453.

Nanopareil, LLC, PCT/US2013/026233, Application No. 13707504. 0, "Extended European Search Report" dated Sep. 30, 2016, 5 pages.

Chinese Patent Office, "First Office Action" issued in connection to Application No. 201380073129.9, dated May 5, 2016, 4 pages.

International Search Report for corresponding PCT Application No. PCT/US2013/026233 dated Apr. 26, 2013.

* cited by examiner

HYBRID FELTS OF ELECTROSPUN NANOFIBERS

This is a Continuation of U.S. Ser. No. 14/000,981 (now issued U.S. Pat. No. 9,604,168), filed Aug. 22, 2013, which is a National Phase Entry of PCT/US13/26233, filed Feb. 14, 2017. The entire contents of both of these patent applications are hereby expressly incorporated herein by reference including, without limitation, the specification, claims, and abstract, as well as any figures, tables, or drawings thereof.

TECHNICAL FIELD

The present invention relates generally to compositions for use in biological and chemical separations, as well as other applications. More specifically, the present invention relates to hybrid felts that are fabricated from electrospun nanofibers with high permeance and high capacity.

BACKGROUND OF THE INVENTION

Microfiber and nanofiber membranes, or "felts", have a variety of different uses for both biological and industrial applications. For example, felts are useful in providing for textile reinforcement, protective clothing, catalytic media, agricultural applications, sensors for environmental, medical, and military monitoring, biomedical applications (e.g., bioseparations, tissue engineering and wound dressings), electronic applications (e.g., capacitors, transistors and diodes), and space applications (e.g., solar sails and backing structure for space mirrors). Microfiber and nanofiber felts are particularly well suited for purifying biological substances, such as proteins, nucleic acids, carbohydrates, bacteria, viruses, cells, and the like. They are useful in all fluid applications, both liquid and gaseous.

The biopharmaceutical therapeutics industry is expanding as more and more biopharmaceuticals are approved for sale. In addition, biologically based diagnostic tools are widely used to perform high throughput, sensitive diagnostic testing of various disease states. For both therapeutics and diagnostics, biological substances (e.g., recombinant proteins, monoclonal antibodies, viral vaccines, and nucleic acids) must be efficiently produced and purified for use.

Conventional purification methodologies include the separation of desired biological substances from byproducts and other contaminants using, for example, packed microbeads for adsorption/chromatography, ultrafiltration, and precipitation/crystallization. These conventional separation methods provide adequate results for many biological applications, but are limited in terms of yield, processing time and degree of purity. These limitations are primarily due to slow diffusion rates of relatively large biomolecules, which limits the ability of the substance being purified (i.e., the "target substance") to access available binding sites deep within the separation matrix. In addition, these systems can only be used for a limited number of cycles, and some can only be used once.

Ion-exchange (IE) and hydrophobic interaction (HI) adsorption/chromatography are two examples of more robust conventional separation technologies that are widely used for separation of biological substances. They are generally less efficient overall than separation technologies based on specific affinity, such as antibody-based separations, but if separation conditions are carefully selected, they are still useful for purifying many target substances from undesirable byproducts and impurities.

While affinity-based adsorption/chromatography may be more efficient than IE and HI, it is generally more difficult and expensive to manufacture, because of the complexity of producing and purifying biological ligands, such as monoclonal antibodies and nucleic acids. Such ligands are also often very sensitive to environmental conditions (e.g., temperature, pH, ionic strength, etc.) and can easily become deteriorated such that the affinity interaction required for adsorption is destroyed. In addition, the binding interaction is sometimes difficult to disrupt without harsh conditions that may lessen the biological activity and hence the usefulness of the target substance and/or the reusability of the purification media.

Membranes that are useful for purification of biological substances have been described. (See, e.g., Bioprocessing for Value-Added Products from Renewable Resources, Shang-Tian Yang, Ed., Chapter 7.) Recently, membrane adsorption/chromatography using nanometer diameter fibers constructed into mats of controlled thickness (i.e., "nanofiber felts") has shown great promise for use in bioseparations (Todd J. Menkhaus, et al., "Chapter 3: Applications of Electrospun Nanofiber Membranes for Bioseparations", in Handbook of Membrane Research, Stephan V. Gorley, Ed.) Such nanofiber felts are superior to microfiber felts, because pore sizes, affinity characteristics, as well as other performance criteria, can be more precisely controlled.

While previously described single component nanofiber felts have provided promising results, they are often less efficient than would be desirable in terms of stability of the felts, as well as material and time requirements. This is particularly true when the target substance is only present in the starting material to be purified at a low concentration, and contaminants and/or the byproducts of synthesis are abundant. Thus, there exists a need to improve the stability of the felts and the purification efficiency of biological products. The embodiments disclosed below satisfy that need.

SUMMARY OF THE INVENTION

The following simplified summary provides a basic understanding of some aspects of the claimed subject matter. This summary is not an extensive overview, and is not intended to identify key/critical elements or to delineate the scope of the claimed subject matter. Its purpose is to present some concepts in a simplified form as a prelude to the more detailed description that is presented below.

In one embodiment, the present invention is an electrospun hybrid nanofiber felt that is formed from a composite nanofiber and a single component nanofiber. The composite nanofiber may be electrospun from a mixture of derivatized cellulose and a first non-cellulose-based polymer, while the single component nanofiber may be electrospun from a second non-cellulose-based polymer, which may be the same or different from the first non-cellulose-based polymer. Usually, the first and second non-cellulose-based polymers are differentially removable from the nanofiber felt, which means that conditions exist (either using solvents or heat, or a combination of solvent and heat) that result in one of the non-cellulose-based polymers being removed to a greater extent than the other (e.g., 10% difference in removability, or more, such as 20% or 50%.)

The derivatized cellulose in the composite nanofiber may be an organic ester of cellulose, an inorganic ester of cellulose, or an alkylcellulose. The organic ester of cellulose may be cellulose acetate, cellulose triacetate, or cellulose proprionate.

When the derivatized cellulose is an inorganic ester, it may be cellulose nitrate and cellulose sulfate, and when it is an alkylcellulose, it may be hydroxyethyl cellulose or carboxymethyl cellulose.

The first non-cellulose-based polymer may be a synthetic or natural polymer, such as a vinyl polymer, a polyether, an acrylic polymer, a polyester, a polycarbonate, a polyurethane, a polysaccharide (e.g., starch or chitin), a polyamide (e.g., protein or gelatin), polylactide, polyglycolide, or a copolymer thereof.

In one embodiment, the second non-cellulose-based polymer that forms the single component nanofiber is a synthetic polymer, such as a vinyl polymer, a polyamide, a polyimide, a polyester, or a copolymer thereof.

In another embodiment, the present invention is an electrospinning method of making the above-described nanofiber felt that can be described in the following steps: a) separately preparing a composite polymer spin dope and a single component polymer spin dope; b) placing the spin dopes in two different spinnerets; c) applying voltage to each spin dope with an electrode; d) separately electrospinning composite and single component nanofibers from the spinnerets; and e) collecting the solidified nanofibers as either randomly overlaid or partially aligned nanofiber felt.

The nanofiber felt as formed can be further processed by regenerating the derivatized cellulose in the composite nanofiber (i.e., converting it back to cellulose). The method of making the nanofiber felt may also include the additional steps of removing some or all of the non-cellulose-based first polymer from the composite nanofiber. Alternatively or in addition to these steps, the method of making the nanofiber felt may also include the step of surface functionalization of one or more of the polymer nanofibers in the nanofiber felt. Such surface functionalization may entail attachment of an affinity ligand that has specific affinity for a particular target molecule to be purified from a fluid.

In yet another embodiment, the present invention is a method of purifying biomolecules from a fluid that can be described in the following steps: preparing a nanofiber felt according to the method just described; b) flowing the fluid through the nanofiber felt; and recovering the biomolecules from the nanofiber felt.

Other aspects of the invention are found elsewhere in the specification.

DETAILED DESCRIPTION OF THE INVENTION

The present invention relates generally to hybrid felts composed of electrospun nanofibers used, for example, for chemical and biological separations. The hybrid nanofiber felts have a high separation capacity and provide reproducible performance over multiple cycles under both high flow and high pressure. Such nanofiber felts exhibit complex interconnected, three-dimensional porous structures and relatively large surface areas.

In particular, the hybrid nanofiber felts are composed of more than one polymer type (i.e., they are "hybrid" felts.)

The felts of the present invention are composed of more than one polymer type (i.e., they are "hybrid" felts.) This includes hybrid felts made from a combination of single component nanofibers and "composite" nanofibers (e.g., the nanofibers are made from a mixture of two or more materials) into the "hybrid" felt. For the "composite" nanofiber, the "backbone polymer" is a derivatized cellulose, and the first non-cellulosic polymer is capable of being removed from the fiber/felt by exposing it to an elevated temperature or chemical solvents, or both an elevated temperature and chemical solvents. In some embodiments, the removal of the first non-cellulosic polymer simultaneously converts the derivatized cellulose back to cellulose, i.e., the cellulose is "regenerated."

The nanofibers in the felts of the present invention are manufactured using an electrospinning technique. This refers to the manufacture of fibers based on exposure of an extruded polymer "spin dope" to an electrostatic field which results in elongation of the extruded polymer "jet" into a nanofiber.

These and other exemplary aspects of the invention are explained in greater detail below.

Definitions

In the description that follows, a number of terms are extensively utilized. The following non-limiting definitions provide a clear and consistent understanding of the specification and claims, including the exemplary scope to be given such terms.

When the terms "one," "a," or "an" are used in this disclosure, they mean "at least one" or "one or more," unless otherwise indicated.

The terms "invention" or "present invention" as used herein are intended to be non-limiting and are not intended to refer to any single embodiment of the particular invention but encompass all possible embodiments as described in the specification and the claims.

The term "permeance" as used herein refers to the flux of fluid passing through the nanofiber felt per unit thickness of the felt, per unit pressure drop. Permeance is considered to be "high" if it is above 500 L/(min m$^2$ 10$^5$ Pa).

The term "flux" refers to the flow rate of fluid passing through the nanofiber felt per unit time, per unit of facial area exposed to the flow.

The term "capacity" as used herein refers to the amount of product bound per unit of adsorbent. Capacity for protein adsorption is considered to be "high" if it is above 100 mg of protein/g adsorbent.

The terms "membrane", "felt", and "mat" as used herein are interchangeable and refer to a non-woven or randomly overlaid collection of fibers.

The term "nanofiber felt" as used herein refers to a collection of nanofibers in a substantially planar array, which may also include microfibers added for strength, enhancing flux, etc.

The term "microfibers" as used herein refers to fibers with diameters larger than 1.0 micrometer, and generally between 1.0 micrometer and 1.0 millimeter.

The term "nanofibers" as used herein refers to fibers with diameters smaller than of 1.0 micrometer, and generally between 10 nanometers and 1.0 micrometer, such as between 200 nm and 600 nm.

The term "hybrid nanofiber felt" as used herein refers to a non-woven or randomly overlaid collection of fibers consisting of at least two types of polymers in a combination of single component fibers or composite fibers with either at least one other single component fiber or at least one other composite fiber.

The term "single component nanofibers" as used herein refers to nanofibers produced from a single polymer.

The term "single component nanofiber felt" as used herein refers to the accumulation of many single component nanofibers into a non-woven or randomly overlaid collection of fibers.

The term "composite nanofibers" as used herein are nanofibers produced from at least two different polymers.

The term "moderately elevated temperatures" as used herein refers to temperatures between 24 and 110° C.

The term "differentially removable" as used herein that, when the hybrid nanofiber felt consists of at least two non-cellulose-based polymers, conditions can be selected (elevated temperature and/or solvent exposure) to remove one of the non-cellulose-based polymers to a greater degree (at least 10% different, and up to 100% vs. 0%) than the other non-cellulose-based polymer.

The term "solvent" as used herein refers to any single component liquid or mixture of liquids capable of dissolving one or more components of the nanofiber felt.

The term "spin dope" as used herein refers to the polymer solution that is used in the electrospinning process.

The term "electrospinning" as used herein refers to the application of electric forces to the spin dope to form the nanofibers.

The term "thermally stable" as used herein means that the polymer does not disintegrate in the temperature range from 50-110° C.

The term "chemically stable" as used herein means that the polymer is not soluble in solvents such as water or common organic solvents (e.g., alcohols and hydrocarbons), and their mixtures.

Derivatized Cellulose

Cellulose is the structural component found in the cell walls of plants and algae. It is also secreted by some bacteria. As such, cellulose is the most abundant organic compound on Earth. It is derived from D-glucose units linked together into a straight chain polymer via β(1-4) glycosidic bonds. For biological and industrial applications, it is purified from plants, wood pulp or cotton, and converted into many useful substances, such as paper, cellophane, rayon, biofuels, etc. The usefulness of cellulose can largely be attributed to its physical properties. It is odorless, hydrophilic, relatively insoluble, exhibits very low non-specific binding, and it is biodegradable.

While cellulose-based separation media have many advantages, they unfortunately suffer from being chemically unstable (i.e., they degrade) in strong acids and bases. Additionally, the dissolution of cellulose requires the use of special solvent mixtures such as N-methylmorpholine-N-oxide (NMMO) and water, or lithium chloride and N,N-dimethylacetamide. This limits the use of cellulose-based media to operations that do not require harsh regeneration conditions, which are often required in the biopharmaceutical industry to meet strict cleaning regulations required by the FDA.

Cellulose fibers are conventionally produced via wet spinning and involve derivatization of the cellulose beforehand, since it is very difficult to electrospin cellulose directly from solution or melt. In order to prepare cellulose nanofibers, research efforts have been dedicated to electrospinning cellulose derivatives, such as cellulose acetate. Unlike cellulose, cellulose acetate is soluble in many common solvents such as acetone. Cellulose acetate can be electrospun into nanofibers and regenerated cellulose nanofibers can be produced by subjecting the nanofibers to post-spinning treatment of hydrolysis/deacetylation.

Accordingly, in the practice of the present invention, one of the polymers in the hybrid nanofiber felt is derivatized cellulose. Cellulose can easily be derivatized using well known methods by converting the —OH group of the individual glucose units into other moieties with more or less reactivity, varying charges, etc. Such derivatized cellulose species exhibit enhanced stability when exposed to solvents and other desirable physical properties. Many cellulose derivatives are readily commercially available. Exemplary derivatized cellulose species include, for example: organic esters (cellulose acetate, triacetate, propionate, acetate propionate, acetate butyrate); inorganic esters (cellulose nitrate, cellulose sulfate); and alkyl cellulose (hydroxyethyl cellulose, carboxymethyl cellulose).

The hybrid nanofiber felts of the present invention will usually have a majority by mass (i.e. 51% or greater) of derivatized cellulose, such as greater than 60% or 70%.

Non-Cellulose-Based Polymers

While the majority by mass in the hybrid nanofiber felt is derivatized cellulose, incorporation of additional types of fibers within the felts provide functionality needed for applications of the felts. Accordingly, it is desirable to have additional fibers within the felts because they can provide increased mechanical strength to the felt, allow for multiple functionalities to be incorporated into the felt, provide stability to the manufacturing process, and other aspects as explained elsewhere herein. Indeed, it was unexpectedly discovered by the present inventors that including even a small proportion of non-cellulosic-based polymers in the hybrid nanofiber felt improved the electrospinning process and also allowed for tailoring of the finished product for a variety of biological and industrial applications, especially when the hybrid nanofiber felt consisted of both a composite nanofiber and a single component nanofiber.

Synthetic polymer nanofibers (e.g., those produced from vinyl polymers and acrylic polymers) offer a wide range of chemical functionalities for bioseparations and other applications. By combining different polymeric units, the surface chemistry of the resulting fiber can be controlled as part of the electrospinning process, providing direct functionality to the produced nanofiber. As an alternative, and similar to conventional micrometer scale fibers, the surface functionality of polymer nanofibers can be chemically modified post-electrospinning to accommodate specific functionality requirements for various bioseparation applications (discussed below). Functionalization chemistries are well known in the polymer arts. They also generally withstand harsh cleaning regimens associated with bioprocesses. Exemplary functionalization chemistries are also discussed in more detail elsewhere herein.

Synthetic carbon-based adsorptive media and filtration membranes are often much more chemically robust than cellulose-based media, and thus can be used when strong acids and bases are required for cleaning the separation media between uses. Furthermore, hybrid nanofibers that include both cellulose-based and non-cellulose-based polymers (e.g., polyacrylonitrile and polyvinyl alcohol) exhibit even higher specific surface area and greater mechanical strength when compared to single component cellulose or single component synthetic polymer nanofibers. Accordingly, there is an observable synergy when composite nanofibers include both cellulose and non-cellulose-based polymers.

Many polymers have been successfully electrospun into nanofibers, including (1) thermoplastic homopolymers such as vinyl polymers, acrylic polymers, polyamides, polyesters, polyethers, and polycarbonates, (2) thermoplastic copolymers such as vinyl-co-vinyl polymers, acrylic-co-acrylic copolymers and vinyl-coacrylic polymers, (3) elastomeric polymers such as triblock copolymer elastomers, polyurethane elastomers, and ethylene-propylene-diene-elastomers, (4) high performance polymers such as polyimides and aromatic polyamides, (5) liquid crystalline polymers such as poly(p-phenylene terephthalamide) and polyaramid, (6) textile polymers such as polyethylene terephthalate and polyacrylonitrile, (7) electrically conductive polymers such as polyaniline, as well as (8) biocompatible polymers (i.e. "biopolymers") like polycaprolactone, polylactide, chitosan and polyglycolide. As described, the polymer may also be a copolymer of two or more of the above-named polymer species.

Examples of the additional polymers that can be added into the hybrid nanofiber felts are electrospun as single component nanofibers from polyacrylonitrile (PAN), polyimides, polyamides (nylon 6, nylon 6,6, nylon 6,10, etc.), polyesters (polyethylene terephthalate, etc.), as well as copolymers thereof.

Composite Nanofibers

In one embodiment of the present invention, the hybrid nanofiber felt includes a composite nanofiber. This is partly due to the fact that the electrospinning process used to make nanofibers from single component derivatized cellulose solutions can be unstable and result in poor yields, low efficiency (long times and many interruptions), poor quality nanofibers (large size distribution, fragile, etc.) with only a single chemical functionality. Therefore, in order to efficiently make large quantities of high quality nanofiber felts with multiple functionalities, it may also be necessary to combine a cellulose derivative with a non-cellulose-based polymer that stabilizes the electrospinning process.

The non-cellulose-based polymer of the composite nanofibers of the present invention may consist of synthetic carbon-based polymers that are removable from the nanofiber felt by exposing it to an elevated temperature and/or solvents. Exposure of the nanofiber felt to either a mixture of solvents or a combination of elevated temperature and solvents can occur simultaneously or sequentially. The presence of the non-cellulose-based polymer during the electrospinning process also enhances nanofiber stability and other aspects of the process, as explained elsewhere herein.

Synthetic polymer nanofibers (e.g., those produced from vinyl polymers and acrylic polymers) offer a wide range of chemical functionalities for bioseparation applications. By combining different polymeric units, the surface chemistry of the resulting fiber can be controlled as part of the electrospinning process, providing direct functionality to the produced nanofiber. As an alternative, and similar to conventional micrometer scale fibers, the surface functionality of polymer nanofibers can be chemically modified post-electrospinning to accommodate specific functionality requirements for various bioseparation applications (discussed below). Synthetic polymer nanofibers offer a tremendous range of potential functionalization chemistries to serve a wide variety of uses. Such functionalization chemistries are well known in the polymer arts. They also generally withstand harsh cleaning regimens associated with bioprocesses.

Many polymers have been successfully electrospun into nanofibers, including (1) thermoplastic homopolymers such as vinyl polymers, acrylic polymers, polyamides, polyesters, polyethers, and polycarbonates, (2) thermoplastic copolymers such as vinyl-co-vinyl polymers, acrylic-co-acrylic copolymers and vinyl-coacrylic polymers, (3) elastomeric polymers such as triblock copolymer elastomers, polyurethane elastomers, and ethylene-propylene-diene-elastomers, (4) high performance polymers such as polyimides and aromatic polyamides, (5) liquid crystalline polymers such as poly(p-phenylene terephthalamide) and polyaramid, (6) textile polymers such as polyethylene terephthalate and polyacrylonitrile, (7) electrically conductive polymers such as polyaniline, as well as (8) biocompatible polymers like polycaprolactone, polylactide, and polyglycolide.

Exemplary non-cellulose-based polymers for making composite nanofibers include, for example, polyethylene oxide, poly(vinylpyrrolidone), poly(vinyl acetate), poly(vinyl alcohol), polysaccharides (chitin, starch, etc.), polystyrene, and poly(methyl methacrylate).

The non-cellulose-based polymer is normally present in the composite nanofibers in an amount of 49% or less by mass, such as 30%, 25%, etc.

Electrospinning

Electrospinning is a technique that utilizes electric forces alone to drive the spinning process and to produce polymer fibers from solutions or melts. Unlike conventional spinning techniques (e.g. solution- and melt-spinning), which are capable of producing fibers with diameters in the micrometer range (approximately 5~25 µm), electrospinning is capable of producing fibers with diameters in the nanometer range. Electrospun polymer nanofibers possess many extraordinary properties including the small fiber diameter and the concomitant large specific surface area, the high degree of macromolecular orientation and the resultant superior mechanical properties. Additionally, felts made of electrospun polymer nanofibers exhibit controlled pore sizes when compared to nanofibers that are made using other fabrication techniques. Unlike nanorods, nanotubes and nanowires that are produced mostly by synthetic methods, electrospun nanofibers are produced through a "nano-manufacturing process", which results in low-cost nanofibers that are also relatively easy to assemble and process into applications.

In general, the formation of nanofibers is a delicate and complicated balance of three major forces involved in the electrospinning process, including the electrical force, the surface tension, and the viscoelastic force. Among these three forces, the electrical force always favors the formation of the product with the highest surface areas. The surface tension always favors the formation of the product with the smallest surface areas. The viscoelastic force is a force which varies significantly with the evaporation of the solvent and is the main reason preventing the breakup of the electrospinning jet/filament into droplets. When the electrical force is dominant, viscoelastic force works against the electrical force. When surface tension is dominant, viscoelastic force works against surface tension.

Theoretically, the smallest nanofibers are capable of being formed under two conditions: (1) when the excess charge density carried by the electrospinning jet is high, and (2) when the time period is long enough and the viscoelastic force is high enough to prevent the capillary breakup of the jet/filament but low enough to allow the electrical force to effectively stretch the jet. For condition (1), it has been found that the addition of soluble electrolytes to the spin dope (e.g., addition of strong electrolytes such as NaCl to polyethylene oxide aqueous solution) can significantly increase the excess charge density carried by the jet and cause the formation of smaller diameter nanofibers. This method, however, also creates negative effects such as (a) a smaller flow rate and the resulting decrease in nanofibers productivity, and (b) the contamination of the prepared nanofibers by the electrolytes. The removal of the electrolytes without sacrificing the properties of nanofibers may be difficult.

For condition (2), further understanding of jet solidification is required. In general, the jet solidification is closely related to the volatility of solvent. If the solvent volatility is too high, the time period for effectively stretching the electrospinning jet/filament is short. Consequently, fibers with relatively large diameters will be obtained. If the solvent volatility is too low, the electrospinning jet/filament is likely to break up into droplets with the stretching. Consequently, beads and/or beaded fibers will be obtained.

Figure 1:
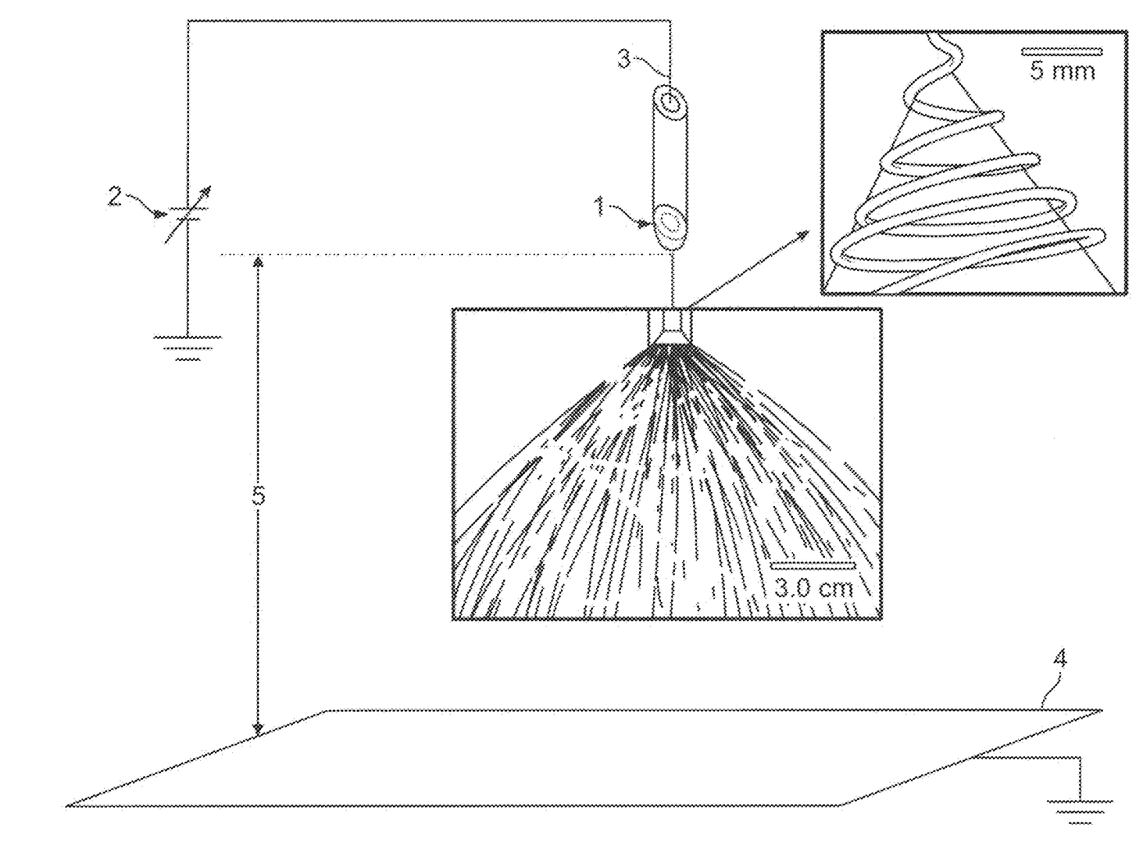
The FIGURE is a schematic representation of the electrospinning process.

The electrospinning process generally includes three steps: (1) initiation of the electrospinning jet/filament and the extension of the jet along a straight trajectory; (2) growth of the bending instability and the further elongation of the jet, which allows the jet to become very long and thin while following a looping and spiraling path; and (3) the solidification of the jet through solvent evaporation or cooling, which leads to the formation of nanofibers. FIG. 1 schematically shows the process of electrospinning (Hao Fong, In Polymeric Nanostructures and Their Applications, Volume 2: Applications: Chapter 11, Electrospun Polymer, Ceramic, Carbon/Graphite Nanofibers and Their Applications, Hari S. Nalwa Editor, American Scientific Publishers, Los Angeles, Calif. (ISBN: 1-58883-070-5), 2007, pp. 451-474.

An exemplary electrospinning process can generally be described as follows:

Step 1:

As shown in FIG. 1, a spin dope (e.g., a polymer solution) is placed in a container with spinneret (1), and DC high voltage (2), usually in the range from 5-40 kilovolts, is applied to the solution through an electrode (e.g., a copper wire)(3). An electrically grounded collector (4) is placed at a certain distance (known as the gap distance)(5) away from the spinneret. The gap distance may range from a few centimeters up to one meter. When the electrostatic field reaches a critical value, and the electric force overcomes surface tension and viscoelastic forces, a jet/filament is ejected and travels straight for a certain distance (known as the jet length).

Step 2:

The jet then starts to bend, forming helical loops. This phenomenon is termed "bending (or whipping) instability." Typically, the bending instability causes the length of a jet to elongate by more than 10,000 times in a very short time period (50 ms or less). Thus, the elongational rate during the bending instability is extremely high (up to 1,000,000 $s^{-1}$). This extremely fast elongational rate can effectively stretch the chain of macromolecules and closely align them along the nanofiber axis.

Step 3:

The jet solidifies, either though evaporation of the solvent or when the melt cools below the solid-liquid transition temperature. The longer the solidification time, the more the jet can be lengthened. The solidification time is related to many factors such as solvent vapor pressure, solvent diffusivity, volumetric charge density carried by the jet, and strength of the applied electrostatic field.

Optional Post-Electrospinning Processing

After solidification of the collected nanofibers, there are certain additional steps that can be performed in order to "customize" the nanofibers for particular uses. Exemplary additional steps are discussed below:

a. Removal of the First Non-Cellulosic Polymer

In some cases, one or more of the polymers, and in particular the non-cellulose-based polymer present in a composite nanofiber, can be removed using elevated heat and/or solvent(s). Removal of the first non-cellulosic polymer provides additional surface area and improved porosity of the remaining cellulose-based polymer. This is because after removal of the non-cellulose-based polymer, the cellulose-based polymer has controlled-sized "pores" left behind where the non-cellulose-based polymer used to occupy space. This additional "void space" provides greater surface area on the resultant nanofiber felt that can, for example, increase adsorptive binding capacity for separations, improve selectivity of size-based separations, and improve throughput from additional porosity. Removing the non-cellulose-based polymer negates the opportunity for multiple functionalities (that had been present within the composite nanofiber) directly present on the remaining cellulose-based polymer nanofiber.

b. Cellulose Regeneration

Following preparation of the "as electrospun" nanofibers, the derivatized cellulose can be converted into cellulose through the process of regeneration. The regenerated cellulose will have the same properties as pure native cellulose described previously. The regeneration process is completed by contacting nanofibers containing derivatized cellulose with, for example, a strong base (e.g., sodium hydroxide), or other solvent. Following the regeneration reaction for conversion to cellulose, the nanofibers can be washed to remove any excess solvent used during the process.

c. Surface Functionalization

After the preparation of hybrid nanofiber felts, the fiber surfaces may be functionalized. Non-limiting examples of functionalization include the addition of ion-exchange groups such as weak or strong acids, and bases (e.g., carboxylic acids and amines), hydrophobic groups such as phenolic compounds, and affinity ligands such as antibodies or enzyme substrates.

For use in bioseparation, the hybrid nanofiber felts of the present invention are ideally biologically inert, meaning that they should resist non-specific binding of insoluble solids such as cells and cellular debris, as well as unwanted interactions with proteins, sugars, nucleic acids, viruses, and other soluble components present in many biologically produced systems.

In addition, nanofiber felts for use in bioseparation should exhibit several qualities: (1) small diameter fibers to allow for the largest amount of specific area (this criterion is most important for adsorption processes and less important for strictly size-based separations discussed below); (2) well controlled and narrow pore size distribution between fibers to allow for even flow distribution during adsorptive applications and for a tight size cutoff for size-based separations; (3) fibers should have excellent mechanical and chemical stability to withstand potentially high operating pressures and harsh cleaning conditions; and (4) fibers should have a well defined and spatially consistent size and chemical composition.

For adsorption processes, where macromolecular products such as proteins, nucleic acids, and viruses are the predominant targets, the extremely large specific surface area associated with nanofiber felts provides an enormous number of potential binding sites for adsorptive bioseparations. Nanofibers can be modified to contain a tremendous number of binding sites and adsorption occurs almost exclusively on the surface of the fibers, which makes the binding sites immediately available without requiring the relatively large target molecule to diffuse internally. Internal diffusion can often limit the capacity for many adsorption processes of bioproducts when using traditional porous resin beads. In addition, because the nanofiber membranes can be made from many different chemistries, the adsorption ligand can be tailored to meet the needs of a particular separation (e.g., ionic, hydrophobic, and affinity). In some cases the ligand can be incorporated into the nanofiber from the source materials during electrospinning, or alternatively the surface can be chemically modified to provide the desired adsorbing agent after producing the nanofiber.

Two of the most important characteristics of the separation operation are that, (1) flow is through micro- and macro-pores of the felt (as opposed to tightly packed resin beads), and (2) that adsorption takes place on the surface of the fibers, where no internal diffusion is required. These factors reduce concerns of high-pressure drops with elevated flow rates, and eliminate the slow intra-particle diffusion required for adsorption within resin beads. It has been shown that the binding capacity of biomolecules to currently available adsorptive felts is similar in magnitude to resin beads, but can operate at processing flow rates over 10 times faster than packed beds. These factors allow for much faster processing times and potentially higher binding levels for purifying valuable biological products. This is highly desirable, especially for large biomolecules (molecular weights greater than 250 kDa, and/or hydrodynamic diameters of 20-300 nm), because they are extremely difficult to purify using packed beds due to the severe mass transfer limitations within the small pores of resin beads.

The surface of the nanofiber felts of the present invention can be modified to provide ion-exchange and hydrophobic interaction chemistry. Simple chemical modification such as sulfonation of polystyrene fibers with sulfuric acid has been used to produce a cation exchange medium. Grafting, atom transfer radical polymerization (ATRP), and plasma treatments have been used to create ion-exchange surface functional groups as well as three-dimensional tethers from a variety of polymeric substrates including polypropylene, polyvinylidene difluoride, polysulphone, and others. Phenyl and butyl groups can also be introduced as hydrophobic interaction ligands. Often times, the surface of polymer membranes must be further modified for greater hydrophilicity to discourage non-specific binding. This has been accomplished by introduction of poly(ethylene glycol) and other polyols onto the surface.

The ion exchange capacity of a hybrid nanofiber felt can also be enhanced by introducing, for example, diethylaminoethyl (DEAE) groups as a weak anion exchange ligand or carboxylic acid as a weak cation exchange ligand.

d. Surface Functionalization with Antimicrobials

In one embodiment of the present invention, the non-cellulose-based polymer is polyacrylonitrile (PAN). Fibrous membranes of PAN have been widely adopted in filtration due to thermal stability, high mechanical properties, and chemical resistivity. Electrospun PAN nanofiber felts have been of particular interest due to properties such as small fiber diameters and the concomitant large specific surface areas, as well as capabilities to control pore sizes among nanofibers and to incorporate antimicrobial agents at nanoscale. Felts consisting of nanofibers with antimicrobial functionality have attracted growing attentions due to the concerns about qualities of purified water and/or filtered air as well as the processing costs. Water and air filters (particularly those operating in the dark and damp conditions) are constantly subject to attacks from environmental microorganisms. The microorganisms (such as bacteria) that can be readily captured by the filters grow rapidly, resulting in the formation of biofilms. Consequently, the buildups of microorganisms on the filter surfaces deteriorate the qualities of purified water and/or filtered air; additionally, they also have the unfavorable effects on the flow of water and/or air.

Moreover, the contaminated filters with biofilms are difficult to clean. Usually, high pressure is required during the operation. This in turn increases the costs. Reported methods incorporate antimicrobial agents (such as N-halamine and silver ions/nanoparticles) directly into spin dopes, thus the molecules/particles of antimicrobial agents are distributed throughout the nanofibers (Xinbo Sun, Lifeng Zhang, Zhengbing Cao, Ying Deng, Li Liu, Hao Fong, and Yuyu Sun. "Electrospun Composite Nanofiber Fabrics Containing Uniformly Dispersed Antimicrobial Agents as an Innovative Type of Polymeric Materials with Superior Anti-Infective Efficacy". ACS Applied Materials and Interfaces, 2(4), 952-956, 2010.)

However, this often leads to process problems, primarily because the high content of antimicrobial agents can seriously affect the process of electrospinning and/or deteriorate the properties of the resulting nanofibers. A potential solution to these problems is to introduce antimicrobial functionality onto nanofiber surfaces after the nanofibers are produced (Lifeng Zhang, Jie Luo, Todd J. Menkhaus, Hemanthram Varadaraju, Yuyu Sun, and Hao Fong. "Antimicrobial Nano-fibrous Membranes Developed from Electrospun Polyacrylonitrile Nanofibers". Journal of Membrane Science, 369, 499-505, 2011.)

It is known that the nitrile (—C≡N) groups in PAN can be chemically converted into amidoxime (—C(NH$_2$)=NOH) groups. The amidoxime groups can coordinate with a wide range of metal ions including silver ions, and the coordinated silver ions can be reduced into silver nanoparticles. Both silver ions and silver nanoparticles are antimicrobial agents with high antimicrobial efficacy.

e. Other Examples

A promising alternative to packed bed chromatography and other separation technologies is the use of the hybrid nanofiber felts of the present invention as selective adsorptive membranes. This style of adsorption utilizes the nanofiber felts as the support for ligands that are used during the selective adsorption process.

Selective adsorption involves "active" surface functionalization of the hybrid nanofiber felt, which allows for direct capture (adsorption) of target substances. Such modification is simplified if the hybrid nanofiber felts include chemical moieties on their surfaces that are relatively simple to chemically modify to provide adsorption sites.

Unlike modifying nanofiber surfaces for ion-exchange and hydrophobic interaction functionality, incorporating affinity ligands onto the nanofiber can be more challenging. Often, the process requires first modifying the surface to create coupling sites for immobilization of the ligand, followed by attachment of the ligand to the active site. Importantly, both the initial surface modification and the coupling of ligand should be robust as not to leach during processing.

In some cases, simple carboxyl groups from grafting methacrylic acid onto the surface can act as the active coupling site by creating a covalent amide bond between the functionalized carboxyl group and an exposed amine group on a protein ligand. Similarly, strong oxidation of cellulose (if controlled properly) can provide aldehyde groups on the fiber surface that can form a covalent attachment to primary amines of a protein (including Protein A and Protein G); especially through the amino acid lysine. In other cases, surface functionalization with a general affinity dye (e.g., Cibacron Blue, capable of binding some proteins) can be coupled directly to a cellulose nanofiber.

More elaborately, bio-active sites for protein ligand immobilization can be incorporated into the nanofiber backbone during nanofelt construction. One example of this is using poly ethylene glycol (PEG) with poly D,L lactide (PDLLA) as a block copolymer. The glycol can be coupled with biocytin (capable of affinity interaction with streptavidin fusion proteins) after electrospinning to create an affinity nanofiber. Similarly, a polycaprolactone (PCL) and poly(D, L-lactic-co-glycolic acid)-b-PEG-NH2 (PLGA-b-PEF-NH2) diblock copolymer can be created containing surface aminated nanofibers for coupling with proteins using a homobifunctional coupling agent. Finally, in some cases it is possible to use intrinsic active sites associated with certain nanofiber matrices. For instance, coupling Concanavalin A (an affinity tag for lectin associated with glycol-proteins and/or other glycolconjugates) to a chitosan-based nanofiber has been successful.

Other techniques for attaching specific ligands to cellulose-based compounds and/or synthetic polymers are known in the chemical arts.

Size Based Separations

As an orthogonal purification mechanism to adsorption, sized based separations are also routinely used in downstream bioprocessing. Depth filtration and microfiltration are common operations used for clarification of fermentation broth, where cells (approximately 1~20 μm) and cellular debris (0.1~1 μm) are removed from the bioreactor slurry. Nanofiltration with membranes is utilized for viral clearance and/or purification of 20~200 nm virus particles, and ultrafiltration is commonly employed for concentration and purification of proteins. In all cases several characteristics of the separation medium are desirable. First, a well defined size cut off is desired to obtain tightly controlled separations. Second, a high porosity material is needed for high throughput processing without excessive pressure requirements to minimize operating time and/or membrane area requirements. And third, chemical and physical robustness is desirable for harsh cleaning conditions and operation under moderate pressures. Nanofiber felts, because they can be produced cheaply in large quantity from mechanically and chemically strong fibers, and with a well controlled pore size among fibers (or as hollow fibers), offer tremendous opportunity as an advanced size-based separation medium. Polymer nanofibers, in general, show the least amount of non-specific binding, but may suffer from being less chemically robust than carbon and ceramic fibers. Ceramic fibers suffer from being brittle and have the potential for large amounts of nonspecific adsorption of biomass/bio-particles with concomitant fouling, but can withstand harsh regeneration conditions.

To date, nanofiber meshes for size-based separations have primarily seen application for isolation of nanometer and micrometer scale bio-particles (or surrogates) by a depth filtration mechanism. The elevated specific surface area of the nanofibers within a filtration mat provides for a more tortuous path and greater chance to intercept a desired particle from solution while maintaining high porosity. Polymer, carbon, and ceramic nanofibers have all been evaluated and were all able to separate the desired particle size from a mixture while maintaining high fluxes. Specifically, electrospun nanofibers made from polyvinylidene fluoride (PVDF) and Nylon 6 were capable of removing polystyrene particles between 0.5~10 Ceramic nanofiber meshes have perhaps been used most extensively. One example shows that a combination of large titanate nanofibers with smaller boehmite nanofibers were capable of very high fluxes (1000 L/m2·h) with relatively low pressure driving force (20 kPa) and could remove virtually all particles larger than 60 nm from a solution. It should be noted that many applications of micro and nano depth filtration also rely on chemical adsorption of particles to the surface, which nanofibers are easily capable of and can be manufactured to specifically adsorb a desired impurity.

Nanofelt Construction/Configuration

By utilizing fibers with diameters in the sub-micron to nanometer range (1~1000 nm, referred to as "nanofiber" felts), the available surface area within a given bed volume for potential binding will be greatly increased, by as much as two orders of magnitude. By controlling the pore size of nanofiber felts, the pressure drop and hydrodynamic flow characteristics can also be controlled and made to be as efficient as microfiber felts.

Furthermore, the pore sizes among fibers in the felt normally have a tight pore size distribution (greater than 90% of the nanofibers fall within the range from 100 nm to 500 nm) to discourage channeling and retain only those species above a desired size cut-off for filtration operations. Finally, the nanofiber felts are usually mechanically strong enough to operate under conditions of potentially high pressure drops (up to 100 psi) and high flow rates (flux values over 30 L/(min·m$^2$)) and chemically robust enough to withstand potentially harsh cleaning regimens (often including strong acids, bases, and organic solvents) without falling apart.

In one embodiment, the nanofiber felts consist of a composite nanofiber (one derivatized cellulose polymer plus one non-cellulose polymer) and a single component nanofiber (non-cellulose based polymer). However, as described above, the hybrid nanofelts of the present invention may be formed from a variety of combinations of polymers and nanofibers. Examples of these include, for example:

- A composite nanofiber felt, wherein all of the nanofibers in the felt consist of a single species of composite nanofiber made from a coextruded mixture of a backbone polymer and a first non-cellulosic polymer.
- A nanofiber felt consisting of at least two different single component nanofibers.
- A nanofiber felt consisting of at least one single component nanofiber and at least one composite nanofiber.

In addition to the above-described nanofelt configurations, the nanofelts of the present invention may also include microfibers for added stability, strength, and to tailor other physical characteristics of the felts for use in particular applications. When compared to single-component nanofiber felts, the hybrid nanofiber felts of the present invention exhibit the following exemplary improved properties:

TABLE 1

| Attribute | Performance Indicators | Quantitative Measures |
|---|---|---|
| Durability/Stability/Permeance | Robust and reproducible performance over multiple cycles (with different cleaning agents) and aggressive operating conditions (high flow and high pressure) | Adsorption capacity versus cycle # (less than 10% loss of capacity after 50 cycles) Adsorption kinetics versus cycle # (less than 10% higher adsorption times after 50 cycles) Force withstood prior to mechanical failure (up to 100 psi pressure with liquid flow) Permeance of liquid flow (over 500 L/ (min · m$^2$ · mm · 10$^5$Pa |
| Improved Adsorption Characteristics | Elevated protein adsorption capacity, more favorable equilibrium adsorption mechanisms, and faster protein adsorption kinetics Higher surface area by introducing pores within nanofibers Higher adsorption selectivity | Static adsorption isotherm model (capacity and favorability) (for protein, over 0.2 mg/mg mat) Adsorption kinetics(over 90% equilibrium achieved within 3 minutes). BET surface area analysis (greater than 20 m$^2$/g) Separation factors when purifying mixtures of (bio)chemicals (at least 2-fold purification) |
| Uniform distribution of fiber diameters and pore size | Improved hydrodynamics and reproducible adsorption performance | Visual SEM images(>90% of fiber diameters fall within the range from 100 nm to 500 nm) Flow distribution analysis (binding and non-binding conditions) (Peclet number over 100 for non-binding solute) |

EXAMPLES

Example 1

Preparation of Prior Art Cellulose Acetate Single Component Nanofiber Felt

A cellulose acetate single component nanofiber felt was made as described in: Handbook of Membrane Research, Chapter 3, *Applications of Electrospun Nanofiber Membranes for Bioseparations*, Todd J. Menkhaus, et al, Nova Science Publishers, Inc., edited by Stephan V. Gorley. Cellulose acetate (average molecular weight of ~30,000 g/mol), NaOH, NaCl, acetone, N,N-dimethylacetamide (DMAc) and N,N-dimethylformamide (DMF) were purchased from the Sigma-Aldrich Co. (Milwaukee, Wis.). 2-(diethylamino) ethyl chloride hydrochloride (DAECH) with the purity of 98% was purchased from the Alfa Aesar Co. (Ward Hill, Mass.).

A solution of 15% (mass fraction) cellulose acetate in acetone/DMAc (mass ratio of 2/1) was prepared at room temperature. The solution was added to a syringe. The electrospinning setup included a high voltage power supply and a laboratory produced roller. During electrospinning, a positive high voltage of 15 kV was applied to the needle, and the flow rate of 1.0 mL/h was maintained using a syringe pump. Cellulose acetate nanofibers were collected as a randomly overlaid felt on the electrically grounded aluminum foil that covered the roller. A heating lamp was used to dry the nanofiber felt during electrospinning, and the felt was further dried in a vacuum oven after electrospinning. Overall, the electrospinning process was relatively unstable, with frequent interruptions at approximately 2 hour intervals. The collected cellulose acetate nanofiber felt had a thickness of approximately 225 µm and a mass per unit area of approximately 60 g/m$^2$.

The as-electrospun cellulose acetate nanofiber felts were first hydrolyzed/deacetylated by immersion in a 0.05M NaOH aqueous solution for 24 hours. The products, referred to as regenerated cellulose nanofiber felts, were then rinsed in distilled water three times and dried in a vacuum oven at 60° C. The samples were immersed in a 15% (mass fraction) DAECH aqueous solution for 10 minutes followed by drying at 60° C. The samples were then immersed in a 0.5M NaOH aqueous solution at 90° C. for 10 min. The samples were rinsed in distilled water three times and dried at 60° C. to yield the DEAE anion-exchange cellulose nanofiber felts.

Example 2

Preparation of a Hybrid Nanofiber Felt of CA/PEO Composite Nanofibers and PAN Single Component Nanofibers Cellulose acetate (CA), polyethylene oxide (PEO), chloroform (CHCl$_3$), dimethylformamide (DMF), polyacrylonitrile (PAN), and diethyl amino ethyl chloride were purchased from Sigma-Aldrich Co. (Milwaukee, Wis.).

The spin dopes of PAN and CA+PEO were prepared separately. Briefly, for the preparation of PAN spin dope, the PAN was dissolved in DMF to make a solution. For the CA+PEO spin dope, CA plus PEO in CHCl$_3$/DMF with diethyl amino ethyl chloride was prepared.

During the electrospinning process two syringes loaded with spin dope of PAN or CA+PEO were placed in the opposite side of the laboratory produced roller. Overall, the electrospinning process was very stable and was sustainable for long periods (>48 hours), and the electrospun hybrid nanofibrous mats consisting of CA+PEO composite nanofibers and PAN nanofibers (either self-supporting or supported on medical-grade cotton gauze) was collected on the electrically grounded aluminum foil which covered the roller.

The as-electrospun CA+PEO+PAN hybrid nanofibrous mats were then annealed for 24 h to complete the phase dispersion of CA and PEO. After that, the mats was hydrolyzed/deacetylated by immersion in a NaOH aqueous solution for 24 hrs. The resulting hybrid nanofibrous mats consisting of regenerated cellulose nanofibers and PAN nanofibers were rinsed with distilled water and dried.

Example 3

Preparation of a Hybrid Nanofiber Felt of CA/PVP Composite Nanofibers and PAN Single Component Nanofibers Cellulose acetate (CA), polyvinylpyrrolidone (PVP), chloroform ($CHCl_3$), dimethylformamide (DMF), polyacrylonitrile (PAN), and diethyl amino ethyl chloride were purchased from Sigma-Aldrich Co. (Milwaukee, Wis.).

The spin dopes of PAN and CA+PVP were prepared separately. Briefly, for the preparation of PAN spin dope, the PAN was dissolved in DMF to make a solution. For the CA+PEO spin dope, CA plus PVP in $CHCl_3$/DMF with diethyl amino ethyl chloride was prepared.

During the electrospinning process two syringes loaded with spin dope of PAN or CA+PVP were placed in the opposite side of the laboratory produced roller. Overall, the electrospinning process was very stable and was sustainable for long periods (>48 hours), and the electrospun hybrid nanofibrous mats consisting of CA+PVP composite nanofibers and PAN nanofibers (either self-supporting or supported on medical-grade cotton gauze) was collected on the electrically grounded aluminum foil which covered the roller.

The as-electrospun CA+PVP+PAN hybrid nanofibrous mats were then annealed for 24 h to complete the phase dispersion of CA and PVP. After that, the mats were hydrolyzed/deacetylated by immersion in a NaOH aqueous solution for 24 hrs; the process would also dissolve/remove the PVP from mats. The resulting hybrid nanofibrous mats consisting of regenerated cellulose nanofibers and PAN nanofibers were rinsed with distilled water and dried.

Example 4

Preparation of a Hybrid Nanofiber Felt of CA/PEO Composite Nanofibers and Nylon 6 Single Component Nanofibers Cellulose acetate (CA), polyethylene oxide (PEO), chloroform ($CHCl_3$), hexafluoroisopropanol (HFIP), nylon 6, and diethyl amino ethyl chloride were purchased from Sigma-Aldrich Co. (Milwaukee, Wis.).

The spin dopes of nylon 6 and CA+PEO were prepared separately. Briefly, for the preparation of nylon 6 spin dope, the polymer was dissolved in HFIP. For the CA+PEO spin dope, CA plus PEO in $CHCl_3$/DMF with diethyl amino ethyl chloride was prepared.

During the electrospinning process two syringes loaded with spin dope of nylon 6 or CA+PEO were placed in the opposite side of the laboratory produced roller. Overall, the electrospinning process was very stable and was sustainable for long periods (>48 hours), and the electrospun hybrid nanofibrous mats consisting of CA+PEO composite nanofibers and nylon 6 nanofibers (either self-supporting or supported on medical-grade cotton gauze) was collected on the electrically grounded aluminum foil which covered the roller.

The as-electrospun CA+PEO+nylon 6 hybrid nanofibrous mats were then annealed for 24 h to complete the phase dispersion of CA and PEO. After that, the mats was hydrolyzed/deacetylated by immersion in a NaOH aqueous solution for 24 hrs; the process would also dissolve/remove the PEO from mats. The resulting hybrid nanofibrous mats consisting of regenerated cellulose nanofibers and nylon 6 nanofibers were rinsed with distilled water and dried.

Example 5

Preparation of a Hybrid Nanofiber Felt of CA/PVP Composite Nanofibers and Nylon 6 Single Component Nanofibers Cellulose acetate (CA), polyvinylpyrrolidone (PVP), chloroform ($CHCl_3$), hexafluoroisopropanol (HFIP), nylon 6, and diethyl amino ethyl chloride were purchased from Sigma-Aldrich Co. (Milwaukee, Wis.).

The spin dopes of nylon 6 and CA+PVP were prepared separately. Briefly, for the preparation of nylon 6 spin dope, the nylon 6 was dissolved in HFIP to make a solution. For the CA+PEO spin dope, CA plus PVP in $CHCl_3$/DMF with diethyl amino ethyl chloride was prepared.

During the electrospinning process two syringes loaded with spin dope of nylon 6 or CA+PVP were placed in the opposite side of the laboratory produced roller. Overall, the electrospinning process was very stable and was sustainable for long periods (>48 hours), and the electrospun hybrid nanofibrous mats consisting of CA+PVP composite nanofibers and nylon 6 nanofibers (either self-supporting or supported on medical-grade cotton gauze) was collected on the electrically grounded aluminum foil which covered the roller.

The as-electrospun CA+PVP+nylon 6 hybrid nanofibrous mats were then annealed for 24 h to complete the phase dispersion of CA and PVP. After that, the mats were hydrolyzed/deacetylated by immersion in a NaOH aqueous solution for 24 hrs; the process would also dissolve/remove the PVP from mats. The resulting hybrid nanofibrous mats consisting of regenerated cellulose nanofibers and nylon 6 nanofibers were rinsed with distilled water and dried.

Example 6

Performance Evaluation of the Single Component and Hybrid Nanofiber Felts

Batch adsorption, dynamic adsorption, flow dispersion and permeability studies with the single component nanofiber mats (Example 1) and hybrid nanofiber mats (Examples 2-6), were compared to a commercially available regenerated cellulose adsorptive membrane and a cotton ball. The commercial cellulose membrane and cotton ball underwent the same post electrospinning treatments as the single component nanofiber felt and hybrid nanofiber felt prior to testing.

Batch adsorption experiments were completed to determine Langmuir equilibrium adsorption isotherms. For batch analyses, the single component felt, hybrid felt, commercial cellulose and cotton ball were rinsed with buffer cut into approximately 1 $cm^2$ individual pieces, and weighed. For each medium, ten of the individual pieces (~100 mg) were then placed into 15 milliliter (mL) centrifuge tubes. Stock solution of target protein was prepared at 2.0 mg/mL by mixing a known mass of lyophilized protein with buffer. Appropriate combinations of stock solution and buffer were added to each test tube containing the cut felt pieces, commercial cellulose membrane, or cotton balls to provide a final volume of 14 mL in each tube and an initial protein concentration between 0.0 mg/mL and 2.0 mg/mL protein. A 1.0 mL liquid sample from each of the different initial protein concentrations was immediately taken and UV absorbance measured at 280 nm. The samples were then placed on an end-over-end mixer rotating at approximately 40 revolutions per minute (rpm). After mixing for a minimum of 24 hours, liquid from each sample was removed and the protein concentration was determined by UV-280-nm absorbance with a Genesys 10 UV spectrophotometer purchased from the Thermo Electron Corporation (Madison, Wis.). By difference, protein adsorbed to the felt could be calculated. A tube was also prepared with 2.0 mg protein/mL and no felt to evaluate the potential of protein adsorbing to the tube surface. No adsorption to the tube surface was found. Likewise, controls were monitored to evaluate the potential of leached chemicals that could contribute to UV-280-nm absorbance, and non-specific binding of protein to non-derivatized membrane (following regeneration with NaOH). No leaching or nonspecific binding was observed for any of the samples. Langmuir adsorption isotherms were then prepared and modeling constants ($Q_{max}$ and $K_d$) determined by least-squares regression fit to the equation:

$$Q = \frac{Q_{max}C}{K_d + C}$$

where Q is the adsorbed equilibrium concentration of protein to the membrane (mg/g), $Q_{max}$ is the asymptotic maximum saturation capacity, C is the liquid phase equilibrium concentration of protein (mg/mL), and $K_d$ is the desorption constant (mg/mL). High values of Q and low values of $K_d$ are indicative of highly efficient adsorption processes. Following adsorption analysis, the liquid was decanted away and the felts were washed with 14 mL of buffer along with mixing for 1 hour. After removing the wash solution, buffer with 1M NaCl was added to the tubes, mixed for 1 hour, and liquid sampled for protein concentration by UV-280-nm absorbance. Elution percentage was calculated based on binding amounts found during the adsorption phase of the study.

The results, shown in Table 2, below, indicated that the electrospun hybrid nanofiber felts had the highest capacity, followed by single component cellulose nanofiber felt. Both nanofiber-based adsorption materials had significantly higher saturation capacity at all equilibrium liquid phase concentrations than any of the commercial cellulose-based adsorption mediums. The regenerated cellulose microfiber felts and cotton balls had the lowest binding capacity. The high specific surface area combined with the unique nanofiber felt morphology are attributed to the elevated binding capacity. In all cases quantitative elution of protein could be accomplished.

TABLE 2

Static Binding Results

| Sample Medium | Qmax (mg/g) | Kd (mg/mL) |
|---|---|---|
| Hybrid nanofiber felt | 168 | 0.31 |
| Single component nanofiber felt | 40.0 | 0.30 |
| Commercial cellulose membrane | 33.5 | 0.54 |
| Regenerated cellulose microfiber felt | 14.5 | 0.31 |
| Cotton ball | 15.5 | 0.82 |

Permeabilities of buffer through the single component and hybrid nanofiber felts, and the commercially available regenerated cellulose adsorptive membranes, were measured. Larger permeability values indicate the ability to operate with higher throughput (faster processing time) and/or lower pressure; both of these provide significant benefits to manufacturing processes. A small-scale "coin" membrane adsorption holder was utilized for all experiments. The unit allows for approximately 1.5 cm² of effective filtration area, and is sealed with an O-ring to discourage leakage. Initially, the pressure drop of the system only, with the membrane holder in place, but with no membrane present, was evaluated at flow rates ranging from 2.0 mL/min to 30.0 mL/min. Then layers of each nanofiber felt or commercial membrane were successively added to the unit while measuring pressure drop at different flow rates. One, three, five, seven, and nine layers were evaluated for each felt/membrane. The system pressure drop was subtracted from the measured pressure drop with the felt/membrane in place to calculate permeability of the felt/membrane at each flow rate. A minimum of five flow rates and corresponding pressure readings were made with each different number of layers.

As shown in Table 3 below, permeability of buffer through the stacks of hybrid nanofiber felts was significantly higher than single component felts, and single component nanofiber felt permeability was at least five times higher than that of the corresponding commercial regenerated cellulose samples. Also, for comparison, a 15 cm packed bed of Sepharose Fast Flow was reported by the manufacturer to have a permeability of approximately 7 L/(min m² 10⁵ Pa), which was similar to the functionalized commercial membrane, but much lower than the nanofelts.

TABLE 3

Permeability (L/(min m² 10⁵ Pa))

| Number of Layers | Hybrid nanofiber felt | Single component nanofiber felt | Commercial regenerated cellulose membrane |
|---|---|---|---|
| 1 | 1220 (±110) | 801 (±75) | 148 (±18) |
| 3 | 977 (±76) | 563 (±44) | 92 (±11) |
| 5 | 627 (±47) | 451 (±21) | 32 (±1) |
| 7 | 318 (±23) | 76 (±6) | 19 (±1) |
| 9 | Not determined | 35 (±2) | 7 (±1) |

System dispersion analysis was performed for the hybrid and single component nanofiber felts and the commercial regenerated cellulose adsorptive membranes to determine the degree of axial mixing with different numbers of layers in place. Less axial mixing (better flow dispersion) is desirable to minimize channeling and pre-mature breakthrough during adsorption processes. The same arrangement used for permeability analysis was used for system dispersion tests, except the flow rate was maintained at 1.0 mL/min during the entire process. After equilibrating the stack of felts/membranes with buffer, a 1% (volume fraction) solution of acetone in buffer was added to the system. Online absorbance at UV-280-nm was monitored and the resulting curve was analyzed to calculate the Peclet (Pe) number by least-squares fit of the equation:

$$\frac{C_{out}}{C_{in}} = \frac{1}{2}\left\{1 + \text{erf}\left[\frac{(Pe)^{1/2}(V - V_{50})}{2(VV_{50})^{1/2}}\right]\right\}$$

where $C_{out}$ is the effluent 280-nm absorbance, $C_{in}$ is the inlet 280-nm absorbance, V is the volume of acetone solution added, and $V_{50}$ is the volume when $C_{out}/C_{in}$=0.50. Larger values of Pe were used to indicate the desirable property of being a closer approximation to plug flow (less axial mixing and better flow dispersion).

Table 4 below, summarizes results for the Pe number as determined for different numbers of hybrid and single component nanofiber mats and commercial regenerated cellulose felt/membrane layers. The results indicate that the nanofiber felts produced in this study had comparable hydrodynamics.

TABLE 4

System Dispersion Results

| Number of Layers | Peclet (Pe) Number Hybrid nanofiber felt | Single component nanofiber felt | Commercial regenerated cellulose membrane |
|---|---|---|---|
| 1 | 45.2 | 25.7 | 39.8 |
| 3 | 81.7 | 43.4 | 62.3 |
| 5 | 96.3 | 59.8 | 78.4 |
| 7 | 112.0 | 74.1 | 92.7 |
| 9 | Not determined | 88.2 | 102.2 |

Dynamic breakthrough analyses were completed to evaluate adsorption efficiency when being operated under flow conditions. Higher capacity at a low % breakthrough would indicate a more efficient adsorbent material. The dynamic breakthrough experiments were completed using a Pall Mustang coin holder according to manufacture's recommendations. Nine layers of either the nanofiber felts or the commercial membranes were used in the analyses. All experiments were operated with an AKTA Purifier (GE Healthcare, Piscataway, N.J.) with online measurement of UV-280-nm absorbance, pH, and conductivity, and controlled by Unicorn software version 5.01. Fractions were automatically collected by the system in 0.60 mL aliquots (approximately 2 bed volumes). A minimum of 10 bed volumes were used for equilibration. Step elution to 100% Buffer B (equilibration buffer with the addition of 1.0 M NaCl) was used for each experiment. For all dynamic breakthrough tests the flow rate was maintained at a value of 1.0 mL/min. Protein stock prepared at 1.5 mg/mL in buffer was loaded until 100% breakthrough was achieved. The felt was then washed with buffer for a minimum of 10 bed volumes before desorption. All eluent (flowthrough during load, wash, and elution) was collected, weighed to determine volume, and analyzed for protein concentration by UV-280-nm absorbance. Protein mass balance was then calculated based on volume loaded and all fractions collected during the process.

The ultimate practical evaluation for any adsorption system is dynamic breakthrough analysis, a combination of equilibrium binding capacity, adsorption kinetics, and system dispersion. It is also a direct application of capacity for a flow through mode of operation where the bound molecule does not need to be selectively eluted from other impurities.

Table 5 below, shows dynamic binding capacity of protein at 10% breakthrough on the nanofiber felts and the commercial regenerated cellulose adsorptive membranes. Dynamic capacity was substantially higher for the hybrid nanofiber mats compared to any other adsorption medium evaluated. In addition, elution results indicated that within experimental uncertainty, elution of protein was complete for each adsorption system, and overall mass balance showed no losses.

TABLE 5

Dynamic Binding Results

| Sample Medium | 10% Breakthrough capacity (mg/g) |
|---|---|
| Hybrid nanofiber felt | 122. |
| Single component nanofiber felt | 26.9 |
| Commercial cellulose membrane | 20.9 |
| Regenerate cellulose microfiber felt | Not Determined |
| Cotton ball | Not Determined |

The examples set forth above are provided to give those of ordinary skill in the art a complete disclosure and description of how to make and use embodiments of the compositions, and are not intended to limit the scope of what the inventors regard as their invention. Modifications of the above-described modes (for carrying out the invention that are obvious to persons of skill in the art) are intended to be within the scope of the following claims. All publications, patents, and patent applications cited in this specification are incorporated herein by reference as if each such publication, patent, or patent application was specifically and individually indicated to be incorporated herein by reference.

What is claimed is:

1. An electrospun hybrid nanofiber felt comprising: a composite nanofiber and a single component nanofiber, wherein the composite nanofiber comprises a mixture of a derivatized cellulose and a first non-cellulose-based polymer, and wherein the single component nanofiber comprises a second non-cellulose-based polymer, wherein the first and second non-cellulose-based polymers are differentially removable from the nanofiber felt, wherein one or more of the nanofibers are surface functionalized.

2. The nanofiber felt according to claim 1, wherein the composite nanofiber is surface functionalized.

3. The nanofiber felt according to claim 1, wherein the single component nanofiber is surface functionalized.

4. The nanofiber felt according to claim 1, wherein the surface functionalization comprises the addition of an ion-exchange group, a hydrophobic group, and/or an affinity ligand.

5. The nanofiber felt according to claim 4, wherein the surface functionalization is an ion-exchange group, and wherein the ion-exchange group is a weak anion exchange group, or a weak cation exchange group.

6. The nanofiber felt according to claim 4, wherein the surface functionalization is a hydrophobic group, and wherein the hydrophobic group is a phenyl group or a butyl group.

7. The nanofiber felt according to claim 1, wherein the composite nanofiber contains less than 49% by mass of the first non-cellulose based polymer.

8. The nanofiber felt according to claim 7, wherein the first and second non-cellulose-based polymers are selected from the group consisting of a thermoplastic homopolymer, a thermoplastic copolymer, an elastomeric polymer, a polyimide polymer, an aromatic polyamide polymer, a liquid crystalline polymer, a textile polymer, an electrically conductive polymer, a biocompatible polymer and copolymers thereof.

9. The nanofiber felt according to claim 7, wherein the first and second non-cellulose-based polymers are selected from the group consisting of a vinyl polymer, a polyether, an acrylic polymer, a polyester, a polycarbonate, a polyurethane, an ethylene-propylene-diene-elastomer, a polyimide, a polysaccharide, a polyamide, a polylactide, a poly(p-phenylene terephthalamide), a polyaramid, a polyethylene terephthalate, a polyacrylonitrile, a polyaniline, a polycaprolactone, a polyglycolide, a polyethylene oxide, a poly(vinylpyrrolidone), a poly(vinyl acetate), a poly(vinyl alcohol), a polystyrene, a poly(methyl methacrylate), a protein, and copolymers thereof.

10. An electrospun hybrid nanofiber felt comprising:
a composite nanofiber and a single component nanofiber; wherein the composite nanofiber comprises a mixture of a derivatized cellulose and a first non-cellulose-based polymer, and wherein the composite nanofiber contains less than 49% by mass of the first non-cellulose based polymer; and wherein the single component nanofiber comprises a second non-cellulose-based polymer, wherein the first and second non-cellulose-based polymers are differentially removable from the nanofiber felt, wherein one or more of the nanofibers are surface functionalized.

11. The nanofiber felt according to claim 10, wherein the composite nanofiber is surface functionalized.

12. The nanofiber felt according to claim 10, wherein the single component nanofiber is surface functionalized.

13. A separation method comprising:
a) flowing a fluid through the nanofiber felt of claim 10; and
b) separating molecules from the fluid.

14. The method of claim 13, wherein the separating step is a size-based separation.

15. The method of claim 13, wherein the separating step is an adsorption-based separation.

16. The method of claim 15, wherein the adsorption-based separation is an ionic separation, hydrophobic separation, or affinity separation.

17. The method according to claim 13, wherein the molecules comprise a one or more of a metal ion, a protein, a nucleic acid, or a virus.

18. The method according to claim 17, further comprising a step:
c) recovering the molecules from the nanofiber felt.

19. The method according to claim 13, further comprising a step:
c) flowing the fluid through a second nanofiber felt of claim 10; wherein the separation process of step a) and separation process of step c) are different.

20. The method of claim 13, further comprising a step:
c) recovering the fluid.

* * * * *

UNITED STATES PATENT AND TRADEMARK OFFICE
CERTIFICATE OF CORRECTION

PATENT NO. : 10,293,289 B2
APPLICATION NO. : 15/434180
DATED : May 21, 2019
INVENTOR(S) : Todd J. Menkhaus and Hao Fong Page 1 of 1

It is certified that error appears in the above-identified patent and that said Letters Patent is hereby corrected as shown below:

On the Title Page (63) Related U.S. Application Data:
DELETE entire paragraph
INSERT --Continuation of application No. 14/000,981, filed Aug. 22, 2013, now Pat. No. 9,604,168, which is a national phase entry of application No. PCT/US2013/026233, filed Feb. 14, 2013.--

In the Specification

In Column 1, Line 7:
DELETE "2017" and
INSERT --2013--

Signed and Sealed this
Ninth Day of July, 2019

Andrei Iancu
*Director of the United States Patent and Trademark Office*

UNITED STATES PATENT AND TRADEMARK OFFICE
CERTIFICATE OF CORRECTION

PATENT NO. : 10,293,289 B2
APPLICATION NO. : 15/434180
DATED : May 21, 2019
INVENTOR(S) : Todd J. Menkhaus and Hao Fong

Page 1 of 1

It is certified that error appears in the above-identified patent and that said Letters Patent is hereby corrected as shown below:

In the Specification

In Column 1, at Line 11, add the following paragraph:
GRANT REFERENCE
This invention was made with government support under Grant Number IIP-1214877 awarded by the National Science Foundation. The government has certain rights in this invention.

Signed and Sealed this
Thirteenth Day of October, 2020

Andrei Iancu
*Director of the United States Patent and Trademark Office*